US00PP35818P2

(12) United States Plant Patent
Ammerlaan

(10) Patent No.: US PP35,818 P2
(45) Date of Patent: May 21, 2024

(54) ***HAWORTHIA X GASTERIA* PLANT NAMED 'OVROCKS12'**

(50) Latin Name: ***Haworthia pumila* x *Gasteria carintata* var. *verrucosa***
Varietal Denomination: OVROCKS12

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/445,501

(22) Filed: Sep. 5, 2023

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 5/00; A01H 6/00
See application file for complete search history.

*Primary Examiner* — June Hwu
(74) *Attorney, Agent, or Firm* — Samuel R. McCoy, Jr.

(57) ABSTRACT

A new and distinct *Haworthia* x *Gasteria* plant named 'OVROCKS12' which is characterized by a plurality of foliar rosettes bearing an abundance of long, lanceolate leaves, dark green leaves that are densely covered with small greyed-green protuberances, and arrangement of the foliar protuberances that varies from randomly-place to arranged in irregular transverse lines across the laminar surface. The new variety has shown to be uniform and stable in the resulting generations from asexual propagation.

4 Drawing Sheets

Latin name of the genus and species: The Latin name of the genus and species of the novel variety disclosed herein is *Haworthia pumila* x *Gasteria carinata* var. *verrucosa.*

Variety denomination: The inventive variety of *Haworthia* x *Gasteria* disclosed herein has been given the variety denomination 'OVROCKS12'.

BACKGROUND OF THE INVENTION

Parentage: 'OVROCKS12' is a seedling selection resulting from the controlled pollination of an unnamed *Haworthia pumila* plant (unpatented), the seed parent, with an unnamed *Gasteria carinata* var. *verrucosa* plant (unpatented), the pollen parent. The crossing was made by the inventor in February of 2013 at a commercial greenhouse in Bleiswijk, the Netherlands. In October of 2013, one seedling from said cross was observed to exhibit unique foliage and growth characteristics when compared to the parent plants and all other progenies. After confirming the stability of the unique characteristics first observed, the new plant was selected for commercialization and given the name, 'OVROCKS12'.

Asexual Reproduction: The variety now called 'OVROCKS12' was first asexually propagated by stem cuttings in October of 2013 at a greenhouse in Bleiswijk, The Netherlands and has since been vegetatively propagated through several additional generations. Through these subsequent generations, the unique features of this cultivar are stable and reproduced true to type.

SUMMARY OF THE INVENTION

The cultivar 'OVROCKS12' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS12'. These characteristics in combination distinguish 'OVROCKS12' as a new and distinct *Haworthia* x *Gasteria* cultivar:

1. 'OVROCKS12' exhibits a plurality of rosettes bearing an abundance of long, lanceolate foliage; and
2. 'OVROCKS12' exhibits dark green foliage that is densely covered with small, round, light greyed-green protuberances; and
3. 'OVROCKS12' exhibits arrangement of the foliar protuberances that varies from randomly-place to arranged in irregularly transverse lines across the laminar surface; and
4. 'OVROCKS12' exhibits entire margins bearing foliar protuberances.

BOTANICAL DESCRIPTION OF THE PLANT

Figure 1:
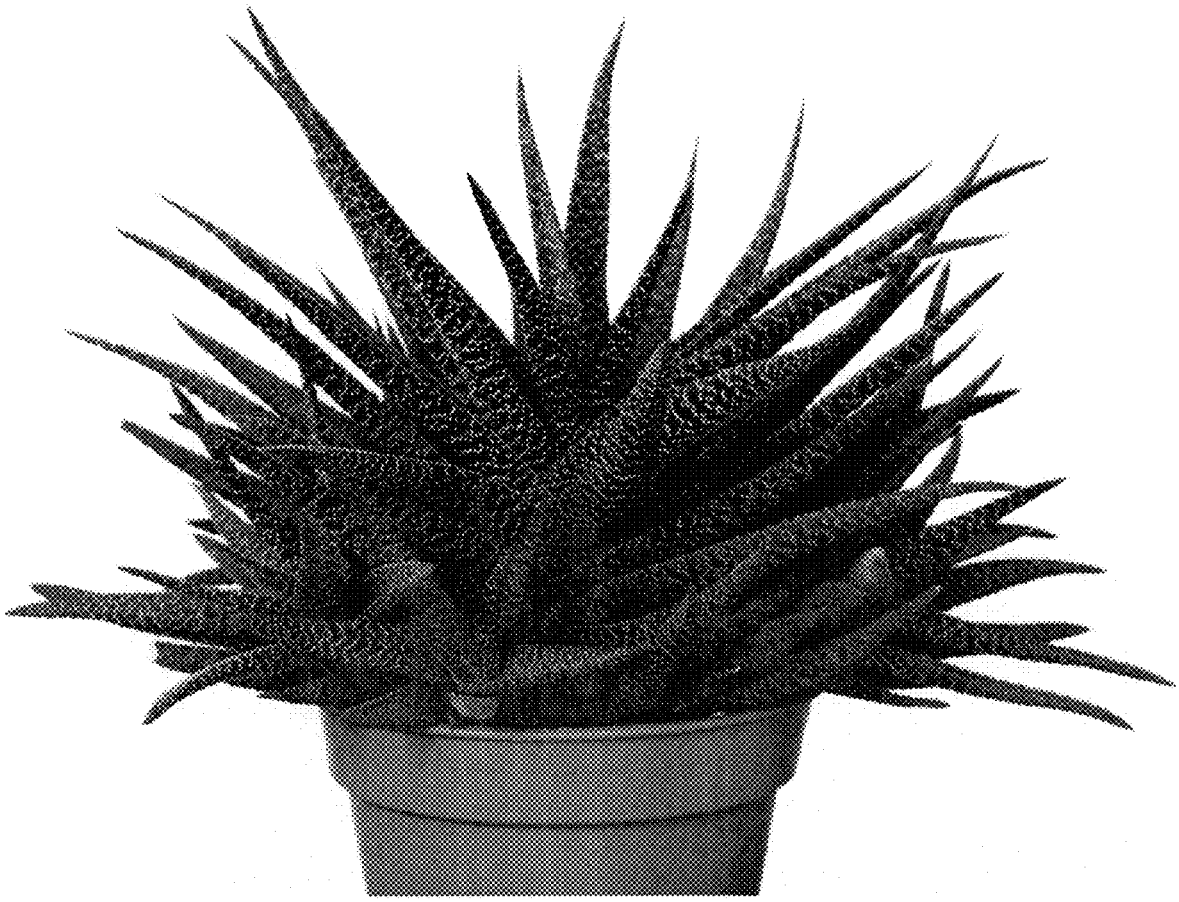
FIG. 1 illustrates, as nearly true as it is reasonably possible to make the same in color photographs of this type, an exemplary plant of 'OVROCKS12' grown in a commercial greenhouse in Bleiswijk, the Netherlands. This plant is approximately 6 years old, shown planted in a 17 cm container.
Figure 2:
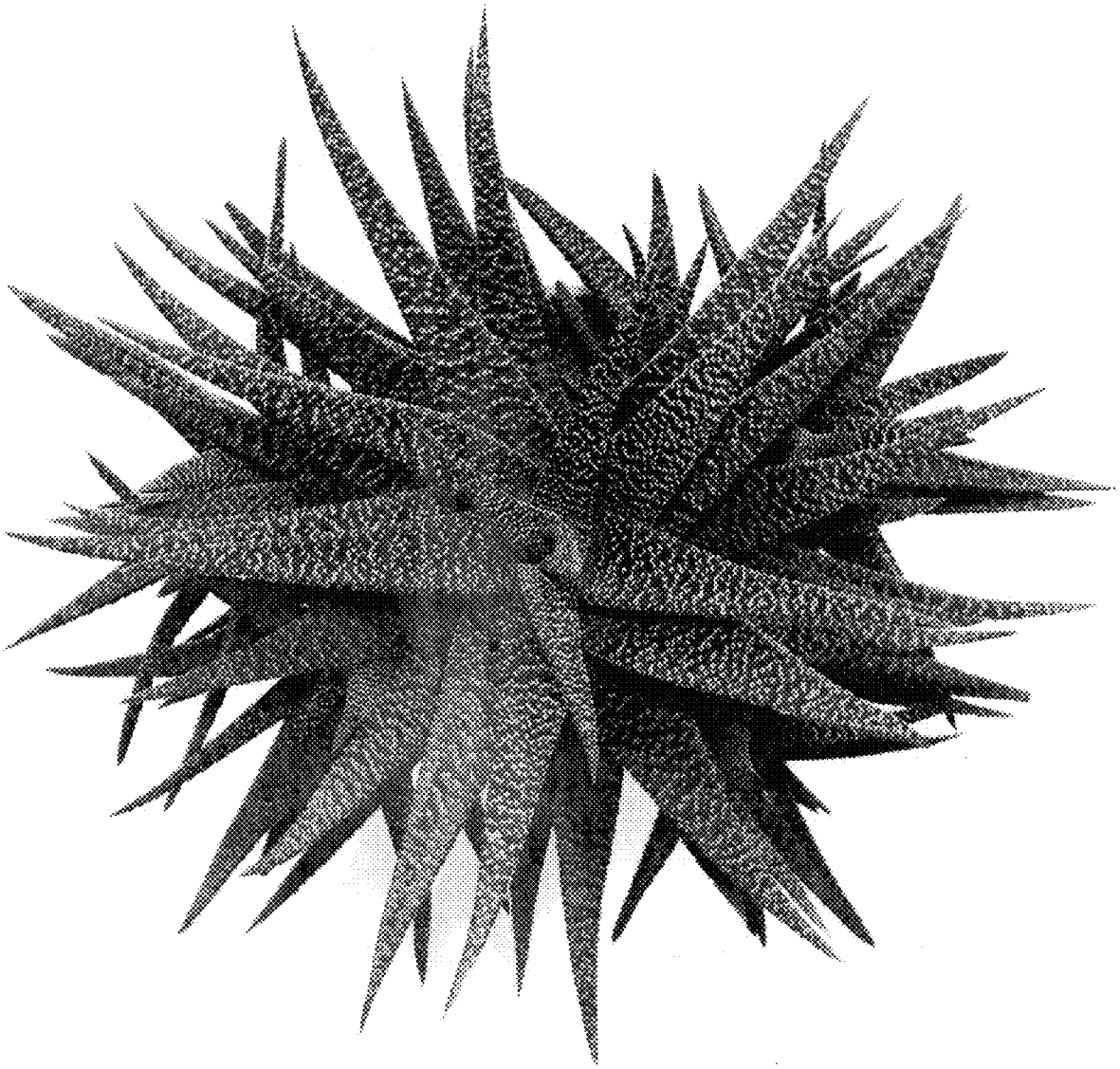
FIG. 2 illustrates, as nearly true as it is reasonably possible to make the same in color photographs of this type, the typical foliage arrangement of 'OVROCKS12'.
Figure 3:
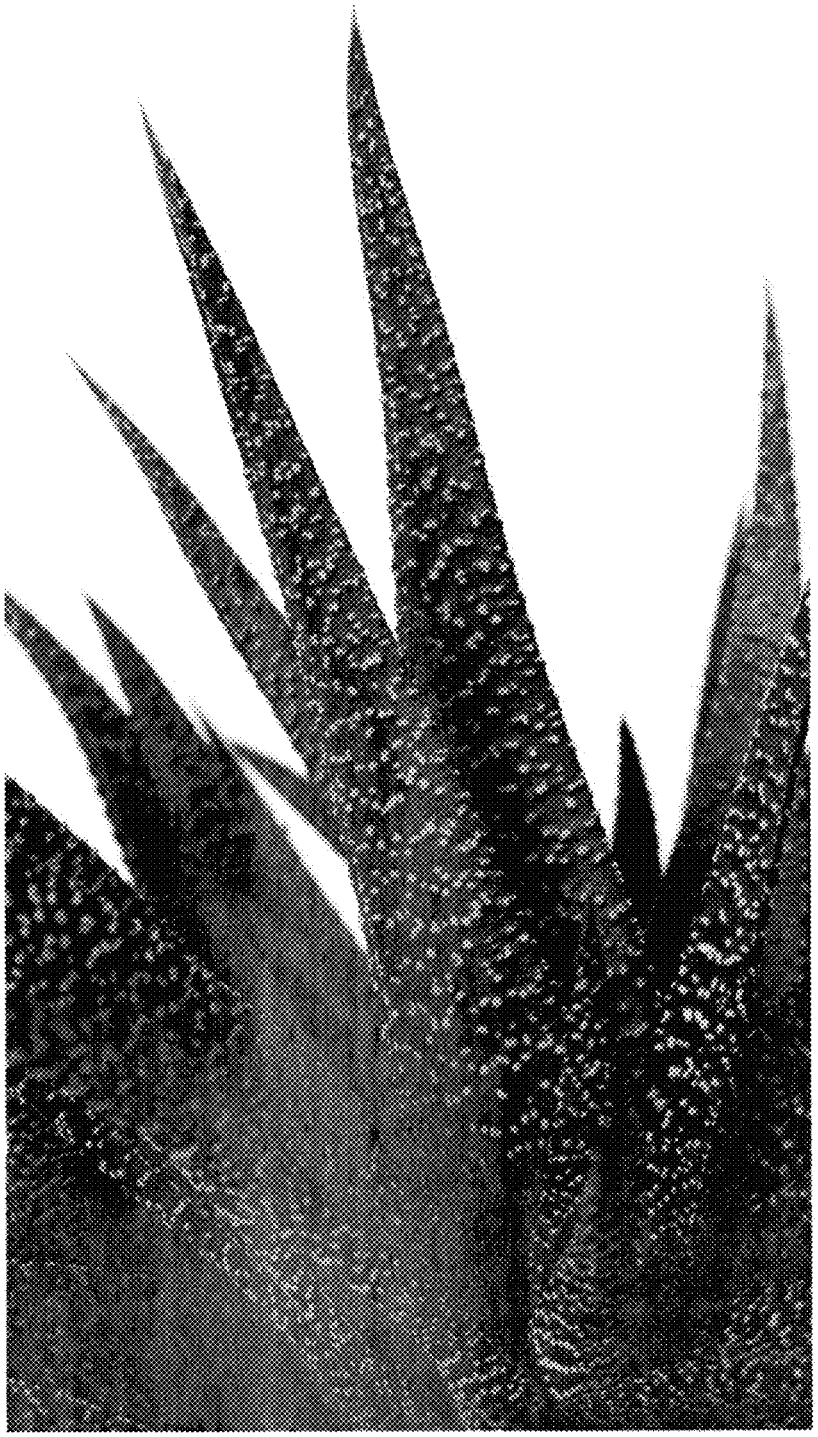
FIG. 3 illustrates, as nearly true as it is reasonably possible to make the same in color photographs of this type, the adaxial surface of the mature foliage 'OVROCKS12'.
Figure 4:
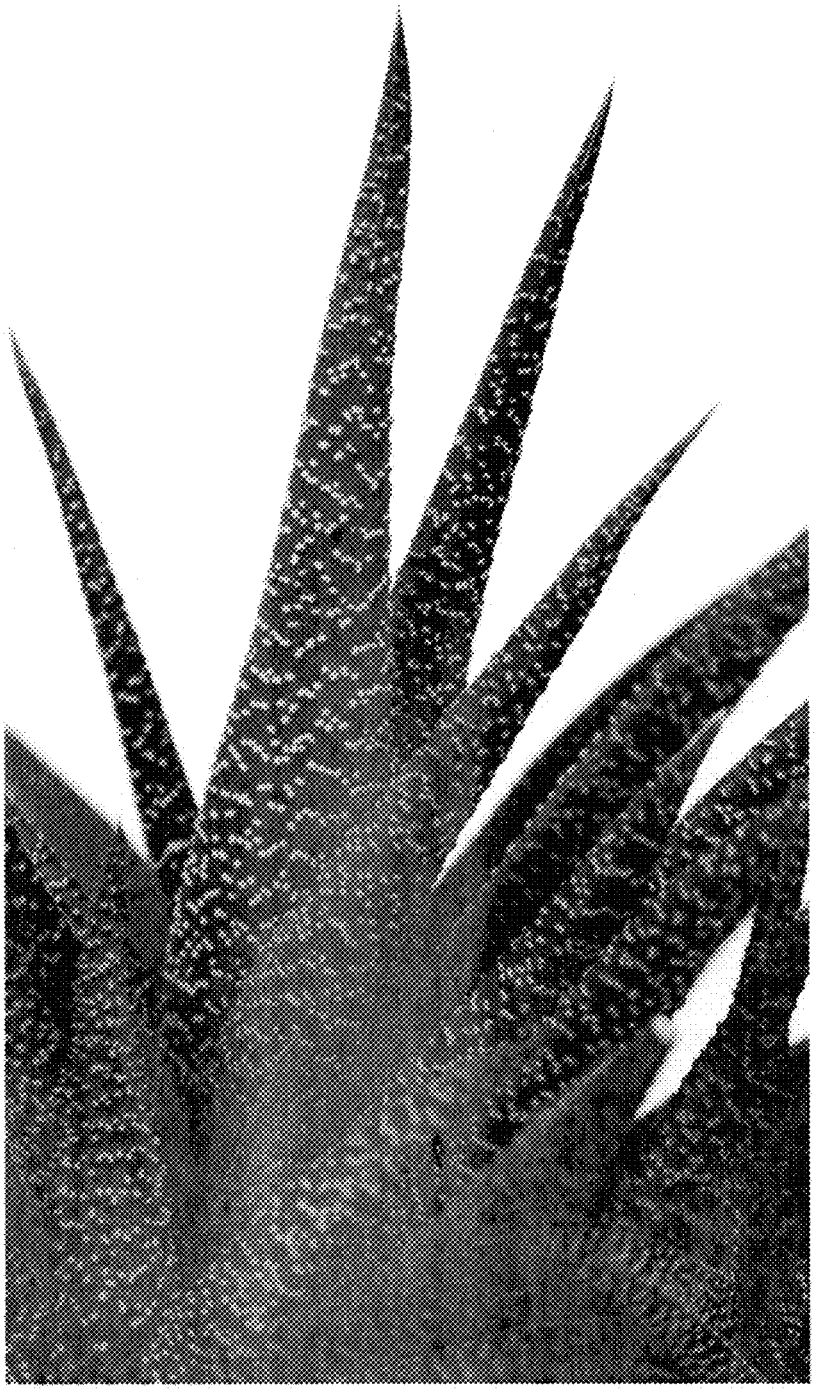
FIG. 4 illustrates, as nearly true as it is reasonably possible to make the same in color photographs of this type, the abaxial surface of the mature foliage 'OVROCKS12'.

The following observations and measurements made in February of 2023 describe averages from a sample set of six specimens of 6 years-old 'OVROCKS12' plants grown in 17 cm nursery containers at commercial greenhouse in Bleiswijk, the Netherlands. Plants were produced using conventional greenhouse production protocols for *Haworthia* sp. and *Gasteria* sp. plants which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS12' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS12' and a comparison with the parents and closest known comparator is provided below.

Plant description:

*Growth habit*.—Succulent perennial with foliage growing in a compact basal rosette; as plants age, secondary rosettes eventually develop at the base of the primary rosette.

*Quantity of secondary rosettes per plant*.—6.

*Plant form*.—Flattened globular.

*Height from soil level to top of foliar plane*.—23.5 cm.

*Plant spread*.—Average of 37.3 cm.

*Plant vigor*.—Highly vigorous; relatively fast growing.

*Propagation*.—Type — Leaf cuttings. Time to initiate rooting — Approximately 5 weeks at an approximate temperature of 21 degrees Celsius. Crop time — Approximately 1 year to produce a marketable plant in a 9 cm container.

*Disease and pest resistance or susceptibility*.—Neither resistance nor susceptibility to typical *Haworthia* sp. and *Gasteria* sp. plants pests and diseases has been observed.

*Environmental tolerances*.—Adapt to, at least, USDA Zones 10 to 12 and temperatures as high as 40 degrees Celsius; low tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Spirally arranged in a basal rosette.

*Division*.—Simple.

*Attachment*.—Sessile.

*Quantity*.—Approximately 40 leaves per rosette.

*Shape*.—Lanceolate.

*Dimensions*.—17.1 cm long, 4.2 cm wide, and 1.2 cm thick.

*Aspect*.—Flat to very slightly concave.

*Attitude*.—Foliage is held upright at and near the center of the rosettes and becomes progressively more relaxed towards the outer whorls of foliage, at an average angle of 30 degrees from horizontal.

*Apex*.—Long, narrowly acute with a soft mucronate tip.

*Base*.—Broad cuneate.

*Margin*.—Entire; bearing foliar protuberances.

*Pubescence and texture, adaxial surface*.—Glabrous, smooth, and densely covered with small, round protuberances; arrangement of the protuberances varies from randomly-place to arranged in irregular transverse lines across the laminar surface; protuberances are approximately 0.1 cm in diameter and height.

*Pubescence and texture, abaxial surface*.—Glabrous, smooth, and densely covered with small, round protuberances; arrangement of the protuberances varies from randomly-place to arranged in irregular transverse lines across the laminar surface; protuberances are approximately 0.1 cm in diameter and height.

*Luster of the adaxial surface*.—Moderately glossy.

*Luster of the abaxial surface*.—Moderately glossy.

*Color*.—Juvenile foliage, adaxial surface — Green, nearest to RHS 139A. The protuberances are colored greyed-green, nearest to RHS 192B. Juvenile foliage, abaxial surface — Nearest to a mixture of green and yellow-green, RHS 139A and 147A. The protuberances are colored greyed-green, distally, nearest to RHS 192B. Mature foliage, adaxial surface — Nearest to a mixture of green and yellow-green, RHS 139A and 147A. Protuberances are colored greyed-green, nearest to in between RHS 191A and 191B. Mature foliage, abaxial surface — Green, nearest to RHS NN137A, transitioning to grey-brown towards the base, nearest to RHS N199A. The protuberances are colored greyed-green, distally, nearest to RHS 192B.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

Comparisons With the Parent Plants

Plants of the new cultivar 'OVROCKS12' differ from the seed parent, an unnamed *Haworthia pumila* plant (unpatented), in the following characteristics described in Table 1 below.

TABLE 1

| Characteristic | 'OVROCKS12' | The seed parent. |
|---|---|---|
| Foliage length. | Longer than the parent. | Shorter than 'OVROCKS12'. |
| General coloration of the foliage. | Darker green, relative to the parent. | Lighter green, relative to 'OVROCKS12', and narrowly margined white. |
| Foliar margins. | Finely dentate; teeth have an average length of 0.5 cm. | Finely crenate, with blunt teeth approximately 0.2 to 0.3 cm. |
| Prominence of foliar protuberances. | Less prominent. | More prominent. |
| Arrangement of foliar protuberances. | Varies from randomly-place to arranged in irregular transverse lines across the lamina. | Arranged in distinct transverse lines across the lamina. |

Plants of the new cultivar 'OVROCKS12' differ from the pollen parent, an unnamed *Gasteria carinata* var. *verrucosa* plant (not patented), in the following characteristics described in Table 2 below.

TABLE 2

| Characteristic | 'OVROCKS12' | The pollen parent. |
|---|---|---|
| Abundance of foliage. | More abundant. | Less abundant. |
| Arrangement of foliar protuberances. | Varies from randomly-place to arranged in irregular transverse lines across the lamina. | Arranged in distinct transverse lines across the lamina. |
| Abundance of foliar protuberances. | More abundant. | Less abundant. |
| Coloration of foliar protuberances. | Greyed-green. | White. |

Comparison With the Closest Known Comparator

Plants of the new cultivar 'OVROCKS12' differ from the most similar variety known to the inventor, x *Gasteraloe* 'Royal Highness' (not patented), in the following characteristics described in Table 3 below.

TABLE 3

| Characteristic | 'OVROCKS12' | 'Royal Highness' |
|---|---|---|
| Foliage length. | Longer than 'Royal Highness'. | Shorter than 'OVROCKS12'. |
| Arrangement of foliar protuberances. | Varies from randomly-place to arranged in irregular transverse lines across the lamina. | Arranged in distinct transverse lines across the lamina. |
| Abundance of foliar protuberances. | More abundant. | Less abundant. |
| Size of foliar protuberances. | Smaller than 'Royal Highness'. | Larger than 'OVROCKS12'. |
| Coloration of foliar protuberances. | Greyed-green. | White. |

That which is claimed is:

1. A new and distinct variety of *Haworthia* x *Gasteria* plant named 'OVROCKS12', substantially as described and illustrated herein.

* * * * *